United States Patent
Kressirer et al.

(10) Patent No.: US 10,040,060 B2
(45) Date of Patent: Aug. 7, 2018

(54) HOLLOW NEEDLE FOR A SAMPLE PIPETTOR

(71) Applicant: Siemens Healthcare Diagnostics Products GmbH, Marburg (DE)

(72) Inventors: Rudolf Kressirer, Kelkheim (DE); Eike Ziechner, Wehrheim (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 386 days.

(21) Appl. No.: 14/031,090

(22) Filed: Sep. 19, 2013

(65) Prior Publication Data

US 2014/0083565 A1 Mar. 27, 2014

(30) Foreign Application Priority Data

Sep. 24, 2012 (EP) .................................... 12185613

(51) Int. Cl.
| | | |
|---|---|---|
| *B01L 3/02* | (2006.01) | |
| *G01N 35/10* | (2006.01) | |
| *A61M 5/32* | (2006.01) | |

(52) U.S. Cl.
CPC .............. *B01L 3/02* (2013.01); *B01L 3/021* (2013.01); *G01N 35/1079* (2013.01);
(Continued)

(58) Field of Classification Search
CPC .... A16M 5/158; A16M 5/162; A16M 5/3286; A16M 5/34; B01L 3/02; B01L 3/0244; G01N 35/1079
USPC .......... 422/511, 512, 546, 564, 501; 73/864, 73/864.01, 864.14, 864.74; 604/19, 44, 604/188, 272
See application file for complete search history.

(56) References Cited

U.S. PATENT DOCUMENTS 2,717,599 A 9/1955 Huber
2,717,600 A * 9/1955 Huber ................. A61M 5/3286
604/164.01
(Continued)

FOREIGN PATENT DOCUMENTS

DE 69827465 10/2005
EP 1420255 5/2004
(Continued)

OTHER PUBLICATIONS

Japanese Office Action of Japanese Application No. JP 2013-191043 dated Aug. 8, 2017.

*Primary Examiner* — Brian R Gordon
(74) *Attorney, Agent, or Firm* — Dugan & Dugan, PC

(57) ABSTRACT

The invention relates to a hollow needle (1) for a sample pipettor in an automated analysis instrument, which sample pipettor is suitable for withdrawing sample liquid from a sealed sample vessel by virtue of the cover or the cap of the sample vessel being pierced by the hollow needle (1). The hollow needle (1) has a substantially straight cylindrical basic shape with a tip (8) for piercing a cover and enables a removal of sample liquid, comparatively less susceptible to errors, from a sample vessel in an automated analysis instrument. In the region of the tip (8) of the hollow needle (1), a number of faces (22, 26, 28, 30) have been introduced in such a way that the radial force components resulting at the respective faces (22, 26, 28, 30) during an axial movement into an elastic material cancel one another.

14 Claims, 4 Drawing Sheets

(52) U.S. Cl.
CPC .... *A61M 5/3286* (2013.01); *B01L 2200/0689* (2013.01); *B01L 2200/14* (2013.01); *B01L 2300/0838* (2013.01); *Y10T 29/49* (2015.01)

(56) References Cited

U.S. PATENT DOCUMENTS

| | | | | |
|---|---|---|---|---|
| 2,748,769 | A * | 6/1956 | Huber | A61M 5/3286 29/445 |
| 3,906,932 | A | 9/1975 | Becton | |
| 5,515,871 | A * | 5/1996 | Bittner | A61M 5/3286 128/898 |
| 5,753,514 | A * | 5/1998 | Karlsson | A61B 10/0045 422/534 |
| 5,868,721 | A | 2/1999 | Marinacci et al. | |
| 5,935,523 | A * | 8/1999 | McCandless | G01N 35/1079 141/330 |
| 6,135,172 | A | 10/2000 | Fere et al. | |
| 7,144,554 | B1 * | 12/2006 | Gulla et al. | 422/521 |
| 7,569,035 | B1 | 8/2009 | Wilmot et al. | |
| 2009/0099535 | A1 * | 4/2009 | Wang et al. | 604/272 |
| 2009/0326485 | A1 * | 12/2009 | Carlyon et al. | 604/272 |
| 2011/0300035 | A1 * | 12/2011 | Taniguchi et al. | 422/509 |
| 2012/0041337 | A1 * | 2/2012 | Ferguson et al. | 600/573 |
| 2013/0118900 | A1 * | 5/2013 | Reimitz | G01N 27/44782 204/450 |
| 2013/0243665 | A1 * | 9/2013 | Hur et al. | 422/512 |
| 2014/0276472 | A1 * | 9/2014 | VanderStek | A61B 17/3421 604/272 |
| 2015/0027241 | A1 * | 1/2015 | Domkofski | G01N 1/14 73/863.81 |

FOREIGN PATENT DOCUMENTS

| | | |
|---|---|---|
| JP | 3009385 U | 4/1995 |
| JP | 2001507134 A | 5/2001 |
| JP | 2004170152 A | 6/2004 |
| JP | 2006514874 A | 5/2006 |
| JP | 2011502603 A | 1/2011 |
| WO | 2004064903 | 8/2004 |
| WO | 2009024522 | 2/2009 |
| WO | 2009060047 | 5/2009 |

* cited by examiner

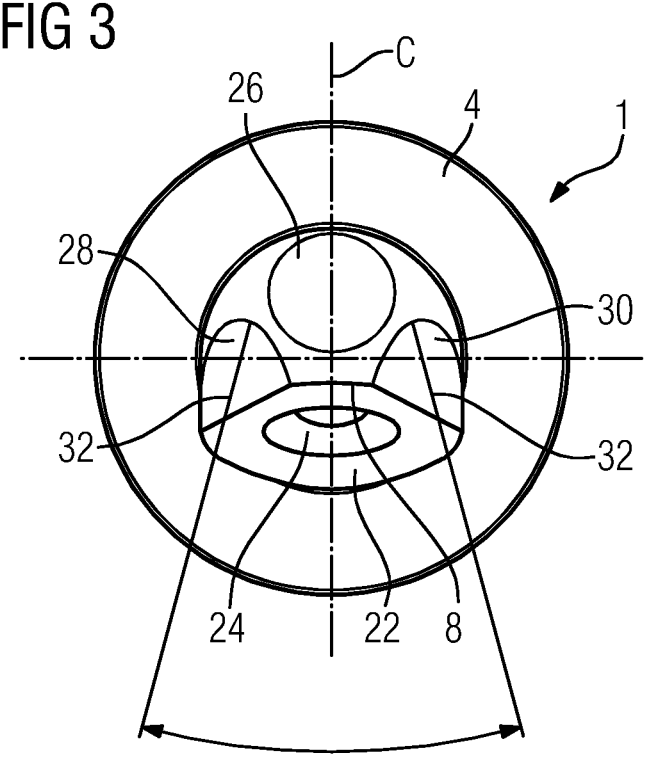
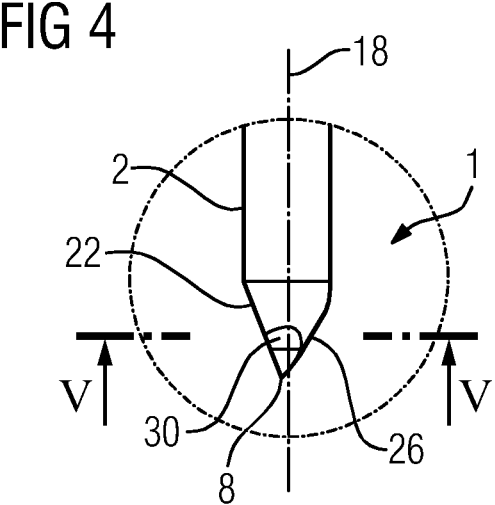

HOLLOW NEEDLE FOR A SAMPLE PIPETTOR

FIELD

The invention relates to a hollow needle for a sample pipettor in an automated analysis instrument, which sample pipettor is suitable for withdrawing sample liquid from a sealed sample vessel by virtue of the cover or the cap of the sample vessel being pierced by the hollow needle.

BACKGROUND

These days, several detection and analysis methods for determining physiological parameters in bodily-fluid samples or other parameters in other biological samples are carried out in an automated fashion in great numbers in corresponding automated analysis instruments. In the field of laboratory diagnostics, the bodily-fluid samples to be analyzed, such as blood, plasma, serum or urine, are provided in sealed sample vessels. The sample vessels are supplied to the analysis instrument individually or in groups, arranged in suitable frames. The sample vessels are usually, by means of a transport system, first of all routed past an identification apparatus, which reads information applied to the sample vessel, e.g. in the form of a barcode, in respect of the identity of the sample and transmits that information to a storage unit. Then, an aliquot of the sample liquid is withdrawn from each sample vessel and transferred into a reaction vessel, in which the analytic test method is then carried out.

Bodily-fluid samples are usually situated in sample vessels made of polymers, less commonly of glass, which are sealed by a cover or a cap made of polymer or by a rubber plug with a thickness of up to 1 cm. Blood, plasma and serum samples are preferably supplied to the analysis instrument in the blood withdrawal tubule. Blood withdrawal tubules usually consist of a transparent polymer and the sealing device is equipped with a specific connector for cannulas. Here, except for in the case of the so-called Sarstedt principle, blood withdrawal tubules are often designed as negative-pressure systems: negative pressure prevails within the sample vessel of this type from the outset. If it is plugged onto the adapter connected to the puncturing cannula, blood is suctioned as a result of this negative pressure. An advantage of this system is that the suctioned up amount of blood is comparatively constant and hence it is also possible to measure out precisely the amount of an anticoagulant (e.g. citrate, EDTA, heparin) introduced into the blood withdrawal tubule in advance. The blood withdrawal tubules are usually sealed by an elastic seal for maintaining the pressure.

In order to withdraw sample liquid from the sample vessels and in order to transfer sample liquid into a reaction vessel, an automated analysis instrument comprises a sample pipettor with a hollow needle. The hollow needle is attached to a transport arm and can thus be moved between at least one sampling position and at least one sample delivery position. At the sampling position, the hollow needle is moved vertically downward, where possible along the central axis of the sample vessel, until the needle tip is immersed in the sample liquid. The immersion is registered with the aid of an appropriate sensor. By generating negative pressure in the hollow needle, sample liquid is suctioned in; the hollow needle is moved vertically upward and subsequently moved horizontally to the sample delivery position. At the sample delivery position, a defined amount of sample is then placed into a reaction vessel. Known hollow needles for such sample pipettors often consist of stainless steel and have a substantially cylindrical basic shape with a central hollow channel, wherein the hollow needle can have axial portions with varying internal and external radii.

If the sample is to be withdrawn from sealed sample vessels, the sample pipettor with hollow needle must be designed in such a way that the vertical downward movement of the hollow needle is carried out with such a force that the sealing device of the sample vessel can be pierced. However, it must be ensured at the same time that the hollow needle is not damaged because there could otherwise be errors during sampling or sample delivery.

In order to keep the amount of force applied for piercing a sealing device of a sample vessel as low as possible, hollow needles provided for this have a comparatively solid design and are usually sharpened. EP-B1-1420255 (FIGS. 34-37; paragraphs 0111-0118) for example describes a hollow needle which has a pyramidal or conical shape at the tip such that an apex is created, at which the force during the downward movement of the hollow needle is focused and a sealing device of a sample vessel, e.g. a rubber cap, can be pierced with comparatively little force being applied.

A further problem when piercing sealing devices with the hollow needle of a sample pipettor consists of the punching-blade effect of the needle, which leads to parts of the perforated sealing device, e.g. rubber crumbs, possibly plugging the pipetting hole of the needle. This problem is solved, inter alia, in DE-T2-69827465 (U.S. Pat. No. 6,135,172) by virtue of the fact that the hollow channel does not open up at the tip itself, but rather laterally on the needle body.

A further problem consists of errors during the sampling being created, in particular, by virtue of the fact that the needle is deflected laterally upon contact with the sealing element of a sample vessel despite careful adjustment and does not pierce along or at least parallel to the central axis of the sample vessel as desired, but rather pierces through the sealing element at an angle. In the worst case, this can lead to the needle touching the inner wall of the sample tubule and possibly even destroying the latter, as a result of which the sample and/or the needle can become unusable and the instrument could possibly be contaminated. Furthermore, it was observed that the sensor signal for the immersion into the sample may be triggered when the needle contacts the inner wall of the sample vessel, even though actual immersion has not yet taken place. This increases the risk of air being pipetted instead of sample liquid.

SUMMARY

This object is achieved by virtue of the fact that a hollow needle for the sample pipettor is provided, which hollow needle has at least two faces in the region of the tip which are arranged in such a way that the radial force components resulting at the respective faces when the tip is introduced into an elastic material, such as e.g. caoutchouc rubber or latex rubber, with an axial movement cancel one another.

The hollow needle preferably has two to eight, particularly preferably four faces in the region of the tip which are arranged in such a way that the radial forces generated at the respective faces cancel one another.

It was found that the unwanted lateral deflection of the hollow needle in a sample pipettor is created by transverse forces acting in the radial direction on the hollow needle when piercing a sealing plug. As a result, the hollow needle is deflected from the vertical direction during further immersion into the sample tubule, and so the inner wall is contacted and there is the risk of pipetting air. The transverse forces are created, in particular, if the needle tip has an asymmetric design.

In accordance with the present invention, the generation of transverse forces is counteracted by appropriate grinding of the needle tip. By grinding the needle tip, planar faces are generated there, wherein the respective faces are introduced in respect of their angle to the axis of the hollow needle and the size of their surface in such a way that radial force components resulting during an axial movement into an elastic material cancel one another. As a result, a deflection of the hollow needle is avoided during the immersion into the blood withdrawal tubule.

The subject matter of the present invention is therefore a hollow needle for a sample pipettor, wherein the hollow needle has a substantially straight cylindrical basic shape with a tip for piercing a sealing device and said needle having at least two faces in the region of the tip such that the radial force components resulting at the respective faces during an axial movement into an elastic material cancel one another.

A preferred embodiment of the hollow needle according to the invention has two faces in the region of the tip, the respective normal of each face lying in a plane with the axis of the hollow needle. In other words: a second face is created for an existing face, the normal of which second face is aligned in such a way that it is able, at least in part, to compensate for the transverse forces of the existing face directly. The surface and the angle of inclination of the face are selected appropriately to this end. As a result of this, it is possible to develop a compensation face for oblique grinding, which compensates the radial forces of the first face of oblique grinding.

The faces are preferably designed in such a way that a predetermined minimum wall thickness of the hollow needle is not undershot. Despite the elastic properties of the commonly employed rubber seals, the hollow needle of a sample pipettor is subject to significant wear due to the high pipetting frequency in modern analysis instruments, and so the hollow needle should be considered to be a consumable and needs to the replaced at regular intervals. An excessive reduction in the wall thickness would impair the stability of the needle tip and reduce the service life. Additionally, openings at positions where this is not desired would be created in the hollow needle as a result of an excessive reduction in the wall faces.

In a further advantageous embodiment, the hollow needle is bent in the region of the tip. This results in a bend in the hollow channel of the needle, and so the outlet of the hollow channel in the case of a corresponding cut is arranged laterally and not in the axial direction. One of the faces is then advantageously introduced in such a way that it at least partly encloses the outlet of the hollow channel in the hollow needle. As a result, the tip of the hollow needle can be positioned further in the direction of the axis of the hollow needle, and so a comparatively more symmetric design and hence a better compensation of the transverse forces is enabled.

The hollow needle has a cylindrical design, preferably a circular cylindrical, quadrilateral or prismatic design. In a particularly preferred embodiment, the cross section of the hollow-needle cylinder is a quadrilateral or a rectangle with concavely ground sides. An advantage of this is that the dynamic and static friction generated during an axial movement of the hollow needle into an elastic material is reduced, as a result of which the hollow needle can be pierced through a rubber plug and be removed therefrom again with comparatively less force expenditure.

As already described, the respective normal of two of the faces advantageously lies in a plane with the axis of the hollow needle. In a further advantageous embodiment, the hollow needle is bent in the region of the tip and one of the faces at least partly encloses the outlet of the hollow channel in the hollow needle.

In an additional or alternative advantageous embodiment, the hollow needle comprises a widening axial portion, which has an axial recess. Since the amount of the withdrawn aliquot from the blood withdrawal tubule is controlled by means of pressure and/or negative pressure, it is necessary to equalize the pressure in the interior of the tubule and the surroundings in order to keep the predetermined amount because otherwise too little an amount of sample would be withdrawn as a result of generated negative pressure during pipetting. As a result of a widening portion, the perforation opening is widened when the hollow needle is immersed. Here, the axial recess is longer than the thickness of the seal such that it extends from the interior up to the exterior. The width and depth of the recess are dimensioned such that the elastic rubber does not completely penetrate into the recess. This creates an air channel which connects the interior and exterior and achieves pressure equalization during the immersion and during the pipetting.

Further subject matter of the present invention relates to a sample pipettor which comprises a hollow needle according to the invention. A sample pipettor according to the invention preferably furthermore comprises a holder, by means of which the hollow needle is attached to a transfer arm which can move between at least one sampling position and at least one sample delivery position. The hollow needle is furthermore connected to a drive which can move the hollow needle in the vertical direction. The sample pipettor preferably has a sensor for detecting the filling level of the sample liquid in the sample vessel.

Further subject matter of the present invention relates to an automated analysis instrument with a sample pipettor which comprises a hollow needle according to the invention. Automated analysis instruments according to the invention have at least one measurement system. Measurement systems which are based on photometric (e.g. turbidimetric, nephelometric, fluorometric or luminometric) or radiometric measurement principles are particularly common. An automated analysis instrument preferably furthermore comprises a storage unit, which stores the measurement results captured by the measurement system. The analysis instrument furthermore comprises an output medium, such as e.g. a monitor, a printer or a network connection, such that the sample-specific measurement values can be made accessible for a user.

The invention furthermore relates to a method for producing a hollow needle for piercing a sealing device of a sample vessel. To this end, at least two faces are introduced into the region of the tip of a hollow needle, which substantially has a straight cylindrical basic shape, in such a way that the radial force components resulting at the respective faces during an axial movement into an elastic material cancel one another.

The at least two faces are preferably introduced by grinding the surface in the region of the tip.

BRIEF DESCRIPTION OF THE DRAWINGS

The invention will be explained in more detail on the basis of a drawing, in which:

FIG. 3 shows a view of the region of the tip of the hollow needle in the axial direction, FIG. 4 shows a lateral view of the region of the tip of the hollow needle.

The same parts have been provided with the same reference signs in all figures.

DETAILED DESCRIPTION

Figure 1:
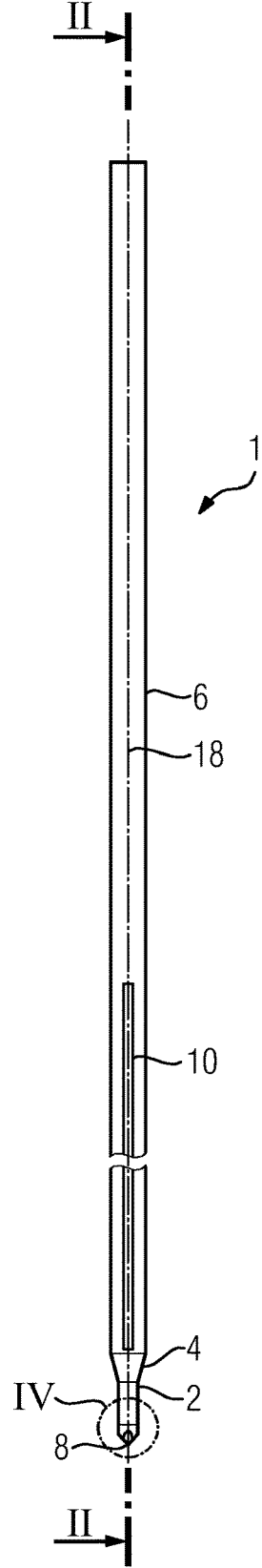
FIG. 1 shows a view of a hollow needle from the direction of the lateral outlet of the hollow channel.

FIG. 1 shows a view of a hollow needle 1. The hollow needle 1 has a substantially circular cylindrical design and has several axial portions 2, 4, 6, proceeding from the tip 8 thereof. Other cylindrical basic shapes are possible here, but the circular cylindrical shape has the best section modulus in all directions. The tip 8 is adjoined by a first axial portion 2, which is ground to form the tip 8 and will be explained in more detail below. The first axial portion 2 has an external diameter of 1.2 mm.

A conical section-shaped second axial portion 4 adjoins the portion 2. The portion 4 widens the external diameter linearly to 2.1 mm. A comparatively long portion 6 with a constant external diameter of 2.1 mm adjoins the second portion 4. A narrow recess 10 extending in the axial direction has been introduced into the region adjoining the second portion. Said recess extends over a comparatively long part of the long portion 6 and, when piercing a seal of a blood withdrawal tubule, forms an air channel which connects the interior and exterior of the tubule and brings about pressure equalization.

Figure 2:
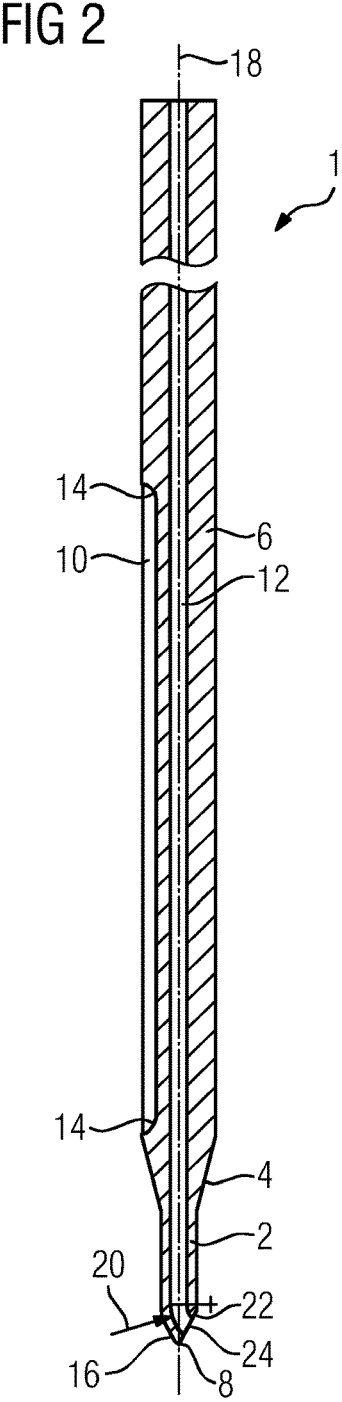
FIG. 2 shows a section through the hollow needle.

FIG. 1 shows the sectional plane II-II, which corresponds to the sectional drawing in FIG. 2. The region IV is illustrated in a magnified fashion in FIG. 4 and FIG. 6.

In addition to the features shown in FIG. 1, FIG. 2 more particularly shows the profile of the recess 10 and the hollow channel 12 in the hollow needle 1. The recess 10 has a length in the axial direction of 134.07 mm, with the recess having a quarter circle-shaped profile at the axial ends 14 thereof, which is caused by the manufacturing process. The recess 10 has a depth of 0.5 mm in the radial direction.

The hollow channel 12 has a constant internal diameter of 0.6 mm over the whole length of the hollow needle 1. A bend 16 of the hollow channel 12, which, with respect to the axis 18, has a bending radius 20 of 1.15 mm, is shown in the region of the tip 8. During the manufacturing process, the hollow needle 1 is initially brought into the substantially circular cylindrical shape with the two different diameters plus internal diameter by drawing; it is subsequently bent at the bend 16 and ground at the face 22. This results in a face 22 which is inclined against the axis 18 in such a way that the tip 8 almost lies on the axis 18. The face 22 encloses the outlet 24 of the hollow channel 12. A flatter section of the face 22 harbors the risk of cutting off rubber material and blocking the hollow channel 12 when piercing the seal.

Now, further faces have been introduced in the region of the tip 8, which faces are selected in respect of inclination and surface in such a way that the force components generated by the respective faces cancel one another in the radial direction. The introduced faces are illustrated in detail in FIGS. 3 to 6. Here, reference is made to the fact that the faces shown in the exemplary embodiment merely constitute a preferred embodiment and can be varied in respect of number, inclination and surface size as long as they meet the criterion of force equalization.

Figure 5:
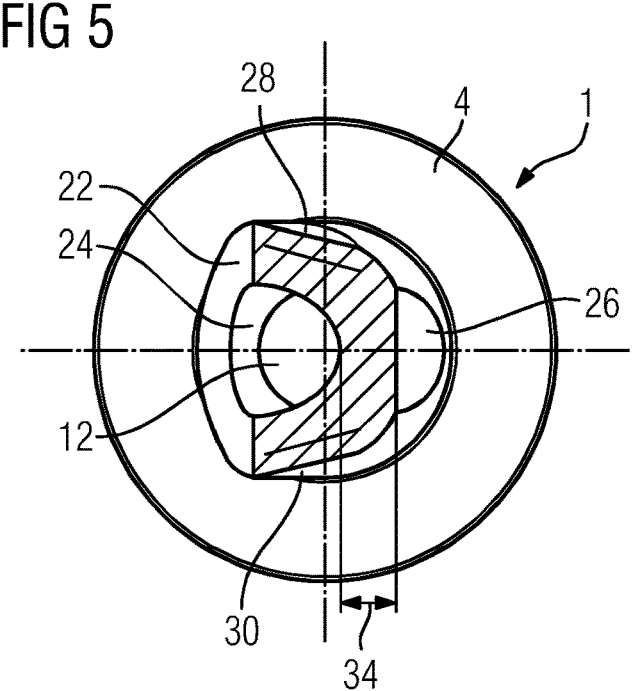
FIG. 5 shows a section through the region of the tip of the hollow needle in the radial direction.

FIG. 3 shows an axial view of the hollow needle 1 with the tip 8, the face 22 and the outlet 24 of the hollow channel 12 (see FIG. 5). The arrangement of the faces is mirror symmetrical in respect of the symmetry plane C. In addition to the face 22, a second face 26 is ground, which is likewise inclined toward the axis 18. The normals of the faces 22, 26 imagined at the respective center of the faces 22, 26 lie in a plane with the axis 18. The face 26 itself has a smaller surface than the face 22. Increasing the face 26 by deeper grinding would reduce the wall thickness below the face excessively, and so a stronger compensation of the transverse forces is not possible here.

Instead, two semicircular further faces 28, 30, which are arranged symmetrically, are applied laterally. In addition to the inclination toward the axis 18, the faces 28, 30 are also inclined in such a way that the cut lines 32 intersect with the radial-azimuthal plane on the side of the axis 18 facing away from the outlet 24 and form an angle of thirty degrees with respect to one another. Overall, this creates a radial force component during piercing which is directed in the same direction as that of the face 26.

During the manufacturing process, it is initially the proportional radial force components during the piercing of the seal that are calculated in each case. The proportion of the force component in the radial direction can be established by means of the angle of inclination of the respective face. The force components established thus are vector-added and the angles of inclination and surface sizes of the faces 22, 26, 28, 30 are selected in such a way that the force components add up to zero.

The grinding established thus is checked in the following by piercing trials. On the one hand, the non-ground surfaces in the region of the tip 8 were not taken into account; on the other hand, these drawn, non-ground surfaces have a completely different frictional behavior than the surfaces 22, 26, 28 and 30. In the piercing trials, grinding is optimized in such a way that the force components generated in practice, which deviate from the theoretically established ones, do in actual fact cancel out and a radial deflection is no longer created. The grinding pattern with inclination, surface and arrangement of the faces 22, 26, 28, 30 established thus is then used directly for producing further hollow needles 1.

Figure 6:
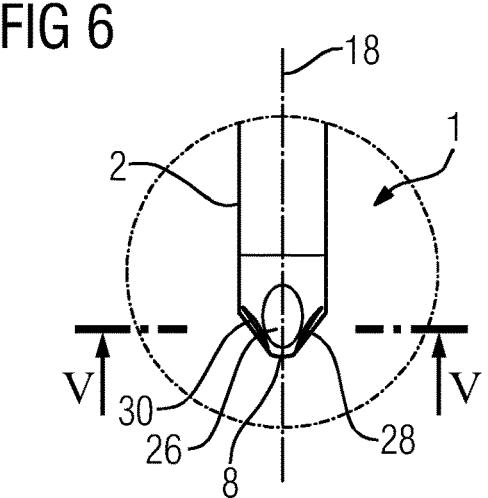
FIG. 6 shows a view of the region of the tip of the hollow needle from the opposite direction compared to FIG. 1

The following FIG. 4, FIG. 5 and FIG. 6 show further illustrations of the hollow needle 1 from different views and are only explained in respect of their peculiarities.

FIG. 4 shows a lateral view of the hollow needle 1. The profile of faces 22 and 26 can be identified here; the face 30 can be seen in the view. The face 28 is covered. The face 26 is inclined by thirty-one degrees with respect to the axis 18, while the face 22, which encloses the outlet 24, is merely inclined by nineteen degrees. The tip 8 is offset by 0.11 mm from the axis 18. In the axial direction, the face 22 extends to a height of 1.41 mm.

FIG. 4 shows the sectional plane V-V, the view of which is illustrated in FIG. 5. Like FIG. 3, FIG. 5 also shows the faces 22, 26, 28, 30 and the inclinations thereof. However, it becomes particularly clear here that the minimum wall thickness 34 has to be maintained, and so the face 26 cannot be ground any deeper.

FIG. 6 shows the rear side view of the hollow needle 1 with the faces 26, 28 and 30. The outlet 24 and the face 22 are covered. It is possible to identify the ellipse-like shape of the face 26. The profile of the tip 8, which is formed in the style of the bent blade by grinding and therefore enables piercing of a sealing device of a sample vessel with lower force expenditure, is also illustrated.

Figure 7:
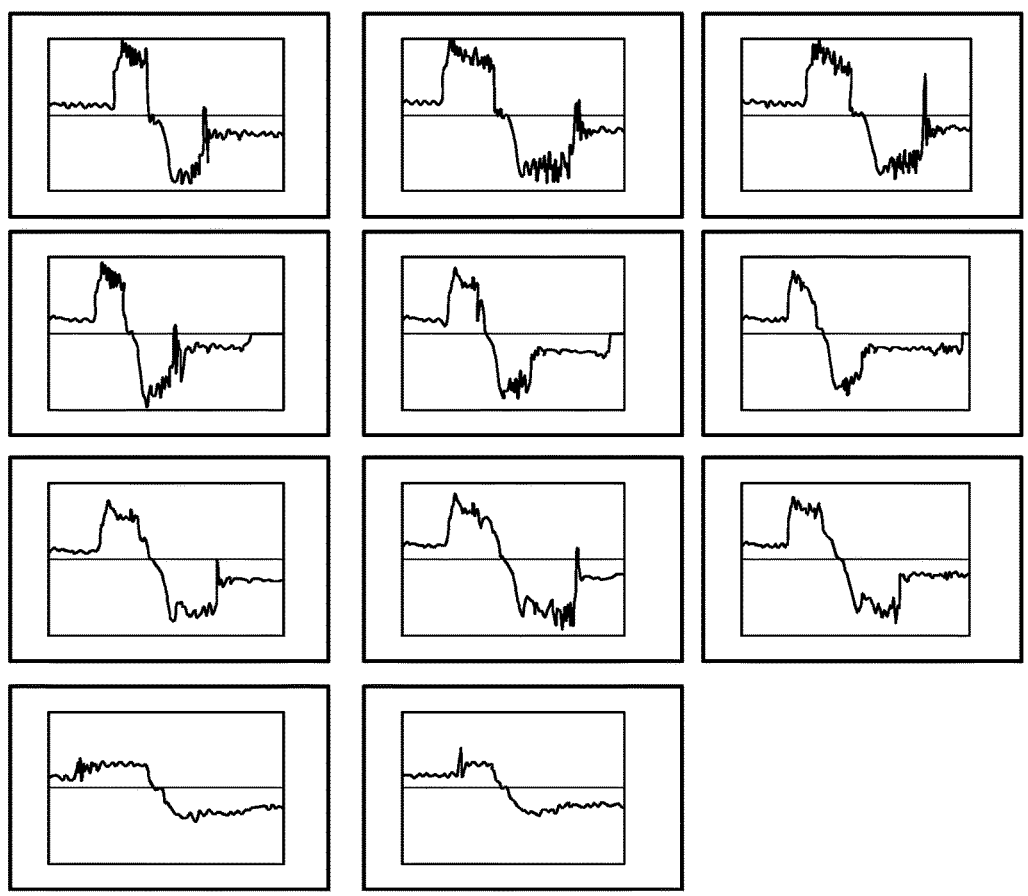
FIG. 7 shows results of trials relating to measuring the force compensation.

FIG. 7 finally shows graphs of the trial logs of several instances of grinding during the above-described optimization process. Here, in an exemplary fashion, the current uptake (respective left-hand Y-axis) of the displacement motor is plotted in each case over time for three different types of grinding (horizontal) and four different blood withdrawal tubules with different sealing devices (vertical). The current uptake corresponds to a force to be applied (respective right-hand Y-axis) when piercing the seal. The hollow needle 1 is driven downward and subsequently returned to the initial position, i.e. the first positive gradient is created during the piercing; the negative deflection is created during the removal of the hollow needle 1 from the seal.

FIG. 7 shows that forces of up to 60 N act. The radial deflection is measured for each piercing attempt and the grinding of the faces 22, 26, 28, 30 is adapted accordingly such that the radial forces cancel one another.

LIST OF REFERENCE SIGNS

1 Hollow needle
2, 4, 6 Portion
8 Tip
10 Recess
12 Hollow channel
14 End
16 Bend
18 Axis
20 Bending radius
22 Face
24 Outlet
26, 28, 30 Face
32 Cut line
34 Minimum wall thickness
II-II Sectional plane
IV-IV Region
C Symmetry plane
V-V Sectional plane

The invention claimed is:

1. A hollow needle for piercing a sealing device on a sample vessel, comprising:
   a needle axis extending in an axial direction of the hollow needle;
   a first axial portion having a first external diameter;
   a second axial portion adjoining the first axial portion, the second axial portion having a conical shape; and
   a third axial portion adjoining the second axial portion; wherein:
   the third axial portion has a second external diameter greater than the first external diameter;
   the first, second, and third axial portions have a hollow channel extending there through at a constant internal diameter, the hollow channel having a bend in the first axial portion;
   the first axial portion has a first face inclined against the needle axis at a first angle of about 19 degrees with respect to the needle axis, the first face forming a tip for piercing the sealing device, the first face having an outlet of the hollow channel arranged laterally with respect to the needle axis;
   the first axial portion has a second face inclined against the needle axis opposite the first face at a second angle of about 31 degrees with respect to the needle axis; and
   the first face and the second face generate respective force components in a radial direction during an axial movement into the sealing device that cancel each other out.

2. The hollow needle as claimed in claim 1, wherein the first axial portion has two to eight faces.

3. The hollow needle as claimed in claim 1, wherein a line normal to the center of the first face and a line normal to the center of the second face lies in a plane with the needle axis.

4. The hollow needle as claimed in claim 1, wherein the first face at least partly surrounds the outlet of the hollow channel.

5. The hollow needle as claimed in claim 1, wherein the second axial portion has a third external diameter equal to the first external diameter adjacent the first portion and has a fourth external diameter equal to the second external diameter adjacent to the third portion.

6. The hollow needle as claimed in claim 1, wherein the tip is offset from the needle axis.

7. A sample pipettor for an automated analysis instrument, the sample pipettor comprising:
   the hollow needle of claim 1; and
   a holder for attaching the hollow needle to a transfer arm.

8. An automated analysis instrument comprising:
   the sample pipettor of claim 7;
   a measurement system; and
   a storage unit to store measurement results captured by the measurement system.

9. The hollow needle as claimed in claim 1, wherein the second face has a smaller surface than the first face.

10. The hollow needle as claimed in claim 1, wherein the first axial portion has two semicircular faces arranged symmetrically about the first face.

11. The hollow needle as claimed in claim 1, wherein the third axial portion has an axial recess extending in the axial direction.

12. The hollow needle as claimed in claim 1, wherein the bend has a bending radius of about 1.15 mm.

13. The hollow needle as claimed in claim 1, wherein the first axial portion has an external diameter of about 1.2 mm.

14. The hollow needle as claimed in claim 1, wherein the third axial portion has an external diameter of about 2.1 mm.

* * * * *